United States Patent
Fäh et al.

(10) Patent No.: US 9,968,425 B2
(45) Date of Patent: May 15, 2018

(54) FEMALE PART FOR FORMING A RELEASABLE CONNECTION TO A MALE PART THAT IS CONFIGURED TO BE FASTENED IN THE MOUTH

(71) Applicant: Cendres+Métaux SA, Biel/Bienne (CH)

(72) Inventors: Mathias Fäh, Solothurn (CH); Mathias Strazza, Meinisberg (CH); Matthias Walther, Münchenstein (CH)

(73) Assignee: CENDRES+METAUX SA (CH)

( * ) Notice: Subject to any disclaimer, the term of this patent is extended or adjusted under 35 U.S.C. 154(b) by 224 days.

(21) Appl. No.: 14/858,079

(22) Filed: Sep. 18, 2015

(65) Prior Publication Data

US 2016/0081776 A1 Mar. 24, 2016

(30) Foreign Application Priority Data

Sep. 19, 2014 (CH) ........................................ 1413/14

(51) Int. Cl.
*A61C 8/00* (2006.01)
*A61C 13/265* (2006.01)

(52) U.S. Cl.
CPC ........ *A61C 8/0093* (2013.01); *A61C 13/2656* (2013.01)

(58) Field of Classification Search
CPC ... A61C 8/0093; A61C 13/2656; A61C 8/005; A61C 8/0089
USPC ........................................ 433/167, 173, 174
See application file for complete search history.

(56) References Cited

U.S. PATENT DOCUMENTS

| | | | | | |
|---|---|---|---|---|---|
| 4,907,969 A | * | 3/1990 | Ward | ...................... | A61C 8/005 433/173 |
| 5,417,570 A | * | 5/1995 | Zuest | ................... | A61C 8/0048 433/172 |
| 5,636,990 A | * | 6/1997 | Stemmann | ........... | A61C 8/0004 433/141 |

(Continued)

FOREIGN PATENT DOCUMENTS

EP  0 867 154 A1  9/1998
EP  0 894 480 A1  2/1999
(Continued)

OTHER PUBLICATIONS

Search Report dated Dec. 19, 2014 issued in corresponding Swiss patent application No. 01413/14.

*Primary Examiner* — Nicholas Lucchesi
(74) *Attorney, Agent, or Firm* — Ostrolenk Faber LLP

(57) ABSTRACT

The female part for forming a releasable connection to a male part (50) that is configured to be fastened in a mouth includes a housing (20), which is configured to be fastened to a dental prosthesis, an insert (1), which is insertable into the housing and rotatable with respect to the housing and in which a portion (51) of the male part can be accommodated, and an adjusting mechanism that is formed in the housing and on the insert and that cause a change in the diameter of the insert when the insert is rotated with respect to the housing. At least one protrusion (5b, 5c) and at least one recess are provided to form the adjusting mechanism. The female part has a locking mechanism, which is formed on the housing and in the insert for defining discretely arranged locking positions, wherein the insert is compressed more in at least one locking position than in at least one other locking position.

22 Claims, 11 Drawing Sheets

(56) References Cited

U.S. PATENT DOCUMENTS

| | | | |
|---|---|---|---|
| 5,685,715 A * | 11/1997 | Beaty | A61C 8/008 |
| | | | 433/173 |
| 6,190,169 B1 | 2/2001 | Bluemli et al. | |
| 6,716,030 B1 * | 4/2004 | Bulard | A61C 8/0048 |
| | | | 433/174 |
| 8,944,817 B2 | 2/2015 | Fischler et al. | |
| 2006/0269903 A1 * | 11/2006 | Bulard | A61C 8/005 |
| | | | 433/174 |
| 2006/0275735 A1 * | 12/2006 | Bulard | A61C 8/0048 |
| | | | 433/174 |
| 2010/0112520 A1 * | 5/2010 | Worthington | A61C 8/0001 |
| | | | 433/169 |
| 2012/0003606 A1 | 1/2012 | Fischler et al. | |
| 2015/0140512 A1 * | 5/2015 | Bachler | A61C 13/2656 |
| | | | 433/201.1 |
| 2015/0297322 A1 * | 10/2015 | Fischler | A61C 8/0062 |
| | | | 433/173 |

FOREIGN PATENT DOCUMENTS

| | | |
|---|---|---|
| EP | 1 021 999 A1 | 7/2000 |
| EP | 2 664 297 A1 | 11/2013 |
| EP | 2 666 437 A1 | 11/2013 |
| WO | WO 2011/027229 A2 | 3/2011 |
| WO | WO 2013/170391 A1 | 11/2013 |

* cited by examiner

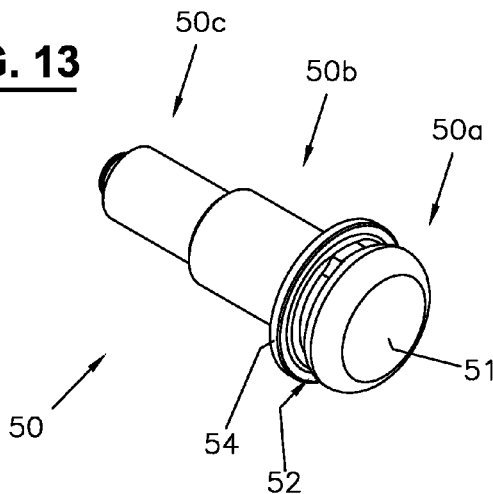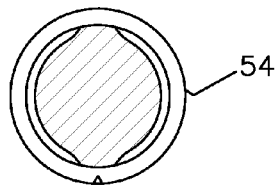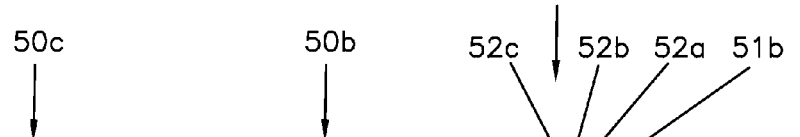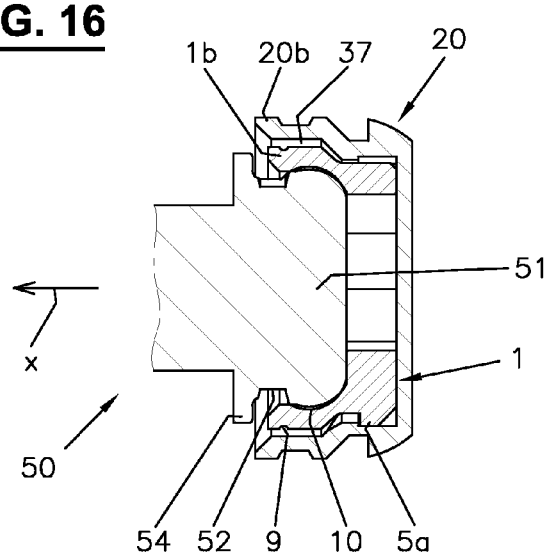

FEMALE PART FOR FORMING A RELEASABLE CONNECTION TO A MALE PART THAT IS CONFIGURED TO BE FASTENED IN THE MOUTH

BACKGROUND OF THE INVENTION

The present invention relates to a female part for forming a releasable connection to a male part that is configured to be fastened in a mouth, comprising a housing that is configured to be fastened to a dental prosthesis and an insert that is insertable into the housing.

Such female parts are used in dental prosthetics to be able to attach a removable denture or some other type of dental prosthesis in a releasable manner in the mouth. With an increase in the duration of use, the holding force with which the female part is retained on the male part may subside due to wear, for example.

In simpler embodiments of the female parts, such as those known from EP 867 154 A1 by the same patent applicant or WO 2011/027229 A2, the original holding force can be restored by replacing the insert. This has the disadvantage that additional replacement parts must be provided and these parts must be changed to set the holding force.

Activatable female parts which make it possible to adjust the holding force are also known. For example, EP 0 894 480 A1 by the same patent applicant describes a female part having a rotatable adjusting ring which acts on the insert. EP 1 021 999 A1 by the same patent applicant has a female part that cooperates with a lamellar insert. This type of female part is designed for continuous adjustability, which makes it difficult to adjust a specific desired force level.

SUMMARY OF THE INVENTION

One object of the present invention is to provide a female part, which permits a defined and simple adjustment of the holding force with which the female part is held on the male part.

This object is achieved by a female part comprising an adjustment mechanism, causing a change in a diameter of the insert when the insert is rotated with respect to the housing, and a locking mechanism, which is formed in the housing and on the insert for defining discretely arranged locking positions, wherein the insert is more compressed in at least one locking position than in at least one other locking position. A simple possibility for adjusting the holding force by rotating the insert with respect to the housing is created by appropriate shaping of the inner side of the housing as well as the outer side of the insert.

The adjustment mechanism is preferably designed, so that when the insert is rotated about the axis of rotation, there is no change in its axial position. This is achieved, for example, by providing at least one undercut and/or by designing the adjusting mechanism without a thread.

Additional features and the advantages thereof are derived from the additional claims as well as the following description.

BRIEF DESCRIPTION OF THE DRAWINGS

The invention is explained in greater detail below on the basis of exemplary embodiments with reference to the figures, in which:

FIG. 13 shows a perspective view of the male part from FIG. 1;

FIG. 14 shows the male part from FIG. 1 in a view from above sectioned at the level of groove 52;

FIG. 15 shows the male part from FIG. 1 in a longitudinal section;

FIG. 16 shows the parts from FIG. 1 joined together in a longitudinal section, showing the male part only partially.

DETAILED DESCRIPTION OF THE PREFERRED EMBODIMENTS

First Exemplary Embodiment

Figure 1:
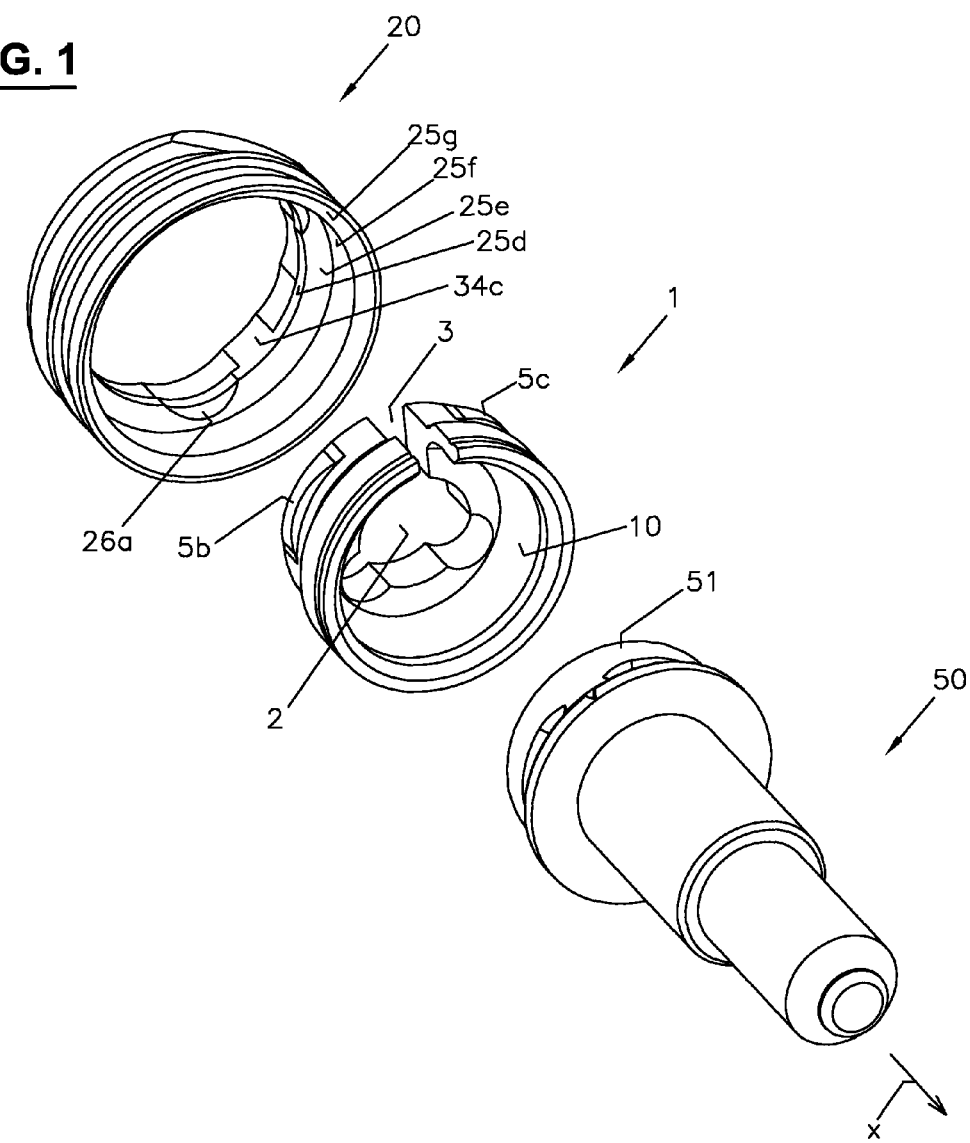
FIG. 1 shows an exploded view of an exemplary male part together with a female part comprising a housing and insert according to a first exemplary embodiment of the invention.

For releasable attachment of a dental prosthesis in the mouth, FIG. 1 shows a connecting set, which has a male part 50 and a female part with a housing 20 and an insert 1. The individual components 1, 20, 50 are shown in FIG. 1 with an offset therebetween in the axial direction x. The components 1, 20, 50 are shifted in this direction x for joining them and taking them apart. The axial direction x is defined by the longitudinal axis of the components 1, 20, 50 and corresponds to the axis of rotation about which the insert 1 can be rotated with respect to the housing 20, as explained further below. In the following description, the axial direction, the longitudinal axis and the x axis are used as synonyms.

Figure 2:
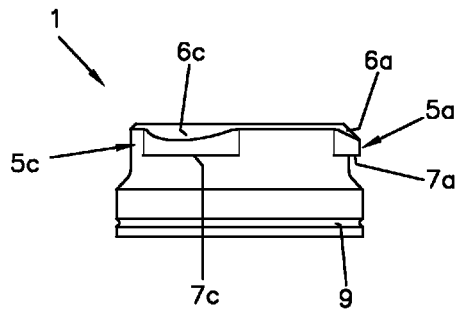
FIG. 2 shows the insert according to FIG. 1 in a side view.
Figure 3:
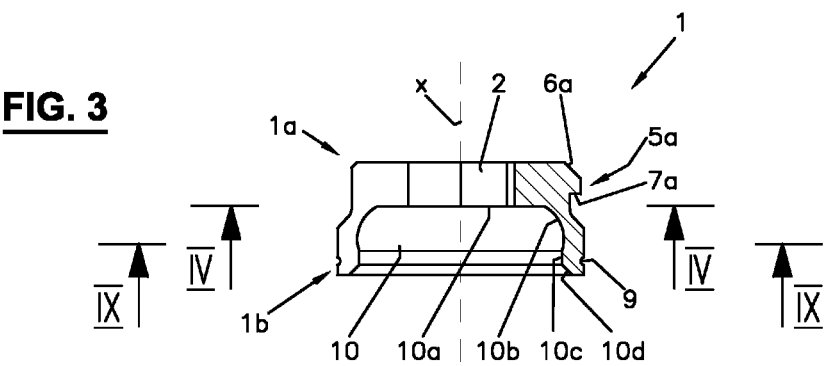
FIG. 3 shows the insert according to FIG. 1 in a longitudinal section, wherein the sectional plane is placed as indicated by line III-III in FIG. 4.
Figure 4:
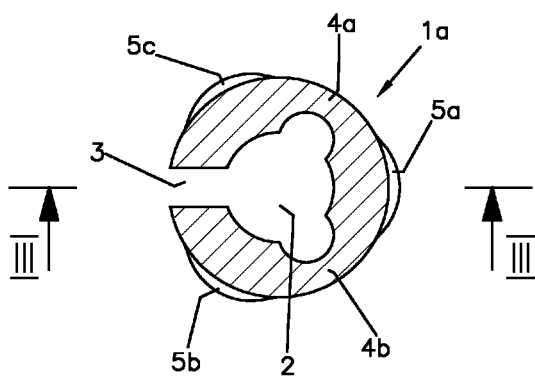
FIG. 4 shows the insert according to FIG. 1 in a cross section, wherein the sectional plane is defined as indicated by the line IV-IV in FIG. 4.

The insert 1, which is shown individually in FIGS. 2 through 4, has a cover element 1a from which a wall element 1b extending around the x axis protrudes. The insert 1 is provided with a through-opening 2 running in the direction of the x axis through the cover element 1a. In addition, the insert 1 has a slot 3 at the side, which passes through the two elements 1a, 1b and opens into the through-opening 2. The insert is thus designed essentially as a C-shaped ring element.

The cover element 1a comprises weakened areas 4a, 4b, where the wall thickness is reduced. Accordingly, the through-opening 2 is shaped so that it extends, as seen in the radial direction, further outward at these weakened areas 4a, 4b than in the remaining part. By providing the weakened areas 4a, 4b, a more uniform compression or expansion of the insert 1 in the radial direction is ensured, for example, the insert 1a is activated—as explained further below—or is fastened to the male part 50.

On the outside, the cover element 1a is provided with protrusions 5a, 5b, 5c, which protrude in the radial direction and are distributed around the circumference of the insert 1.

The respective protrusion 5a, 5b, 5c has a beveled top side 6a, 6c, which facilitates the insertion of the insert 1 into the housing 20 and has a round shape, as seen in the circumferential direction, thereby facilitating further rotation of the insert 1 in the housing 20.

Figure 7:
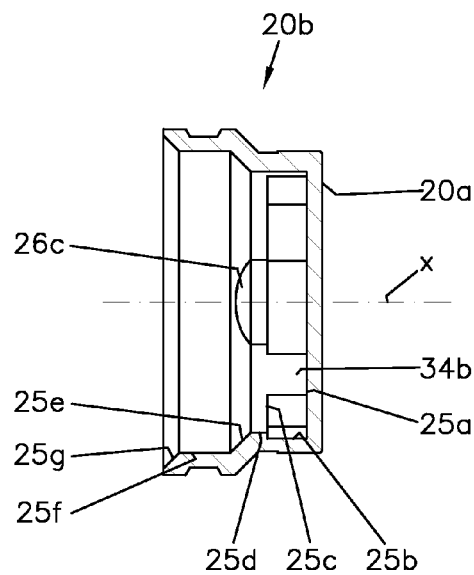
FIG. 7 shows the housing according to FIG. 5 in a section according to line VII-VII shown there.

The bottom side 7a, 7c of the respective protrusion 5a, 5b, 5c serves as a stop surface, which abuts against an inside surface of the housing 20 when the housing 20 and the insert 1 that has been inserted into it are pulled apart (cf. inside surface 25c in FIG. 7). The respective protrusion 5a, 5b, 5c thus defines an undercut shape in the insert 1 to enable retention in the housing 20.

In the present exemplary embodiment, three protrusions 5a-5c which are uniformly distributed in the circumferential direction are provided. A weakened area 4a, 4b or the slot 3 is situated here between two protrusions 5a, 5b, 5c (cf. FIG. 4). However, the elements 3, 4a, 4b may also have a different circumferential position with respect to the protrusions 5a, 5b, 5c. The number of protrusions 5a, 5b, 5c and weakened areas 4a, 4b can be designed according to the intended purpose and may be one, two or more. In a simpler embodiment, the weakened areas 4a, 4b may also be omitted. The slot 3 may also be omitted, so that the wall element 1b forms a closed ring, or one or more notches may be provided in the wall element 1b to form lamellae (cf. notch 3a-3c in the second exemplary embodiment).

The wall element 1b is provided with a groove 9 on the outside. This groove serves to facilitate engagement for an auxiliary instrument for handling the insert 1.

The inside of the insert 1 defines a receptacle 10 for a portion of the male part 50, the head 51 here, and is adapted to its shape accordingly. The inside of the cover element 1a in the present exemplary embodiment is defined by a planar inside surface 10a, which joins a concavely curved round inside surface 10b of the wall element 1b. The inside surface 10b is adjacent to an essentially circular cylindrical inside surface 10c, which is adjacent to an inclined closing surface 10d. Due to this inclination, the receptacle 10 has an inwardly tapering inlet, which facilitates the insertion of the male part 50. The inside of the insert 1 may of course be designed differently than that shown here, depending on the design of the male part, the head of which may be e.g. spherical, conical or of another shape.

Figure 5:
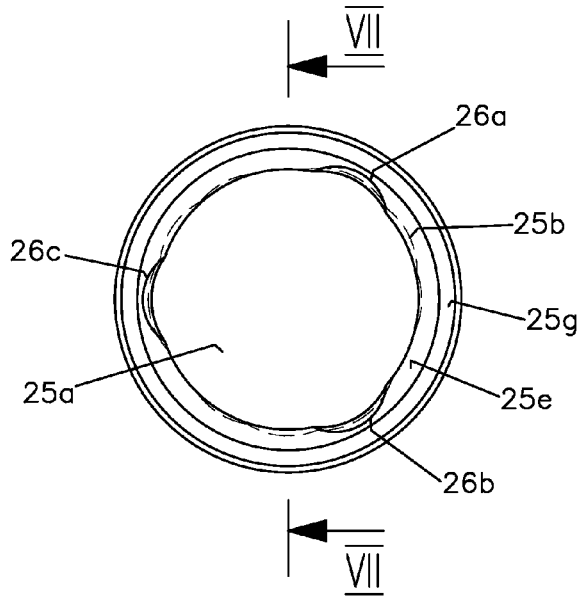
FIG. 5 shows the housing according to FIG. 1 in a view from beneath.
Figure 6:
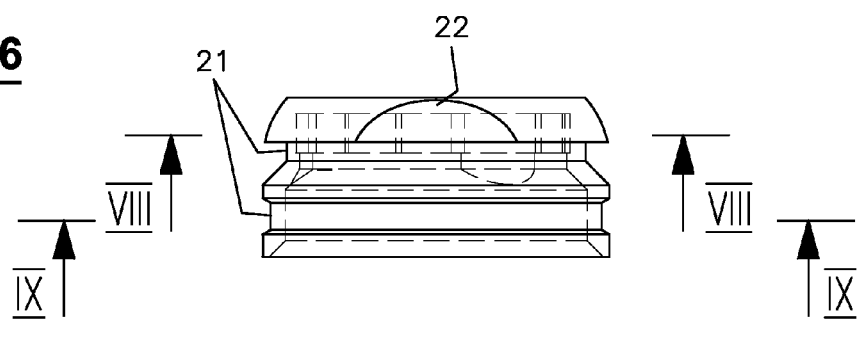
FIG. 6 shows the housing according to FIG. 1 in a view from the side.

The housing 20, which can be attached to the dental prosthesis, for example, a denture, such as by means of polymerization is shown in greater detail in FIGS. 5 through 7. The housing 20 is designed in the shape of a pot and includes a bottom element 20a, which has a flat top side here and from which a circumferential side wall 20b protrudes. The outside of the housing 20 has an undercut shape due to the fact that one or more retention grooves 21 are provided, running around the x axis. A secure connection between the housing 20 and the dental prosthesis can therefore be ensured. In addition, the outside of the housing 20 is designed with a flattened surface on two opposing locations 22 (cf. FIG. 8). Due to the fact that the flat sides 22 are provided, a more rotationally secure hold of the housing 20 is ensured when it is introduced into the plastic of a denture, for example. Depending on the intended purpose, the outside of the housing 20 may also be designed differently.

The interior of the housing 20 defines a receptacle for the insert 1. The inside of the bottom element 20a is defined by a flat bottom 25a. The inside of the side wall 20b comprises circumferential inside surfaces 25b-25g which follow one another in the direction towards the opening of the housing 20 as listed below:

a first inside surface 25b, which is designed for contacting the protrusions 5a-5c on the insert 1,
 a second inside surface 25c, which is arranged transversally to the first inside surface 25b and forms an undercut, so that the protrusions 5a-5c abut against the inside surface 25c when the insert 1 is pulled in the direction of the x axis,
 a third inside surface 25d, which forms the undercut together with the second inside surface 25c and is thus situated at least partially closer to the x axis than the first inside surface 25b, as seen in the radial direction (cf. also FIG. 5, in which the inside surface 25b is concealed and is therefore represented by a broken line),
 a fourth inside surface 25e, which becomes wider to form a transition to an enlarged inside diameter,
 a fifth inside surface 25f, which is formed essentially in the shape of a circular cylinder, and
 a sixth inside surface 25g, which has a bevel or chamfer with an inward inclination and forms the end of the inlet opening of the insert 1.

Figure 10:
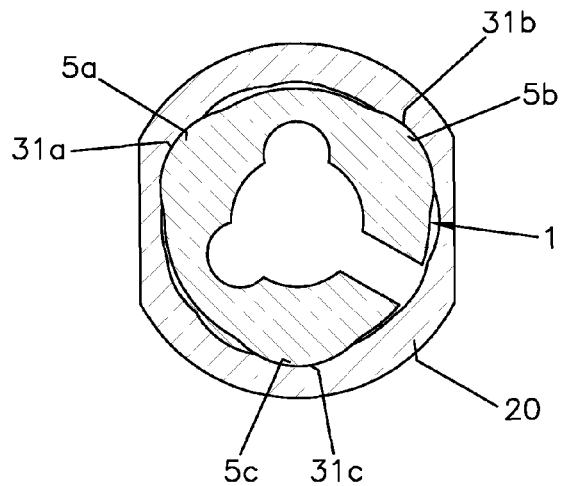
FIG. 10 shows a sectional view of the housing and of the insert according to FIG. 1, which is inserted into the housing and is shown here in the first locking position, wherein the sectional plane is placed as indicated by the line VIII-VIII in FIG. 6.

The fourth inside surface 25e has beveled locations 26a-26c, which have a greater inclination than the remainder of the inside surface 25e. The locations 26a-26c define insertion positions for the protrusions 5a-5c and are thus distributed around the x axis like the protrusions 5a-5c (cf. FIGS. 4 and 5). The positions of the locations 26a-26c here are selected so that the first locking position is reached after insertion of the insert 1 into the housing 20 (cf. FIG. 10).

The second inside surface 25c, which forms the shoulder of the undercut, does not extend continuously in the circumferential direction in the present example but instead is interrupted at locations 34a-34c, which are adjacent to the beveled locations 26a-26c. These locations 34a-34c form a transition, where the third inside surface 25d extends to the bottom 25a (cf. FIGS. 1, 7 and 8).

Figure 8:
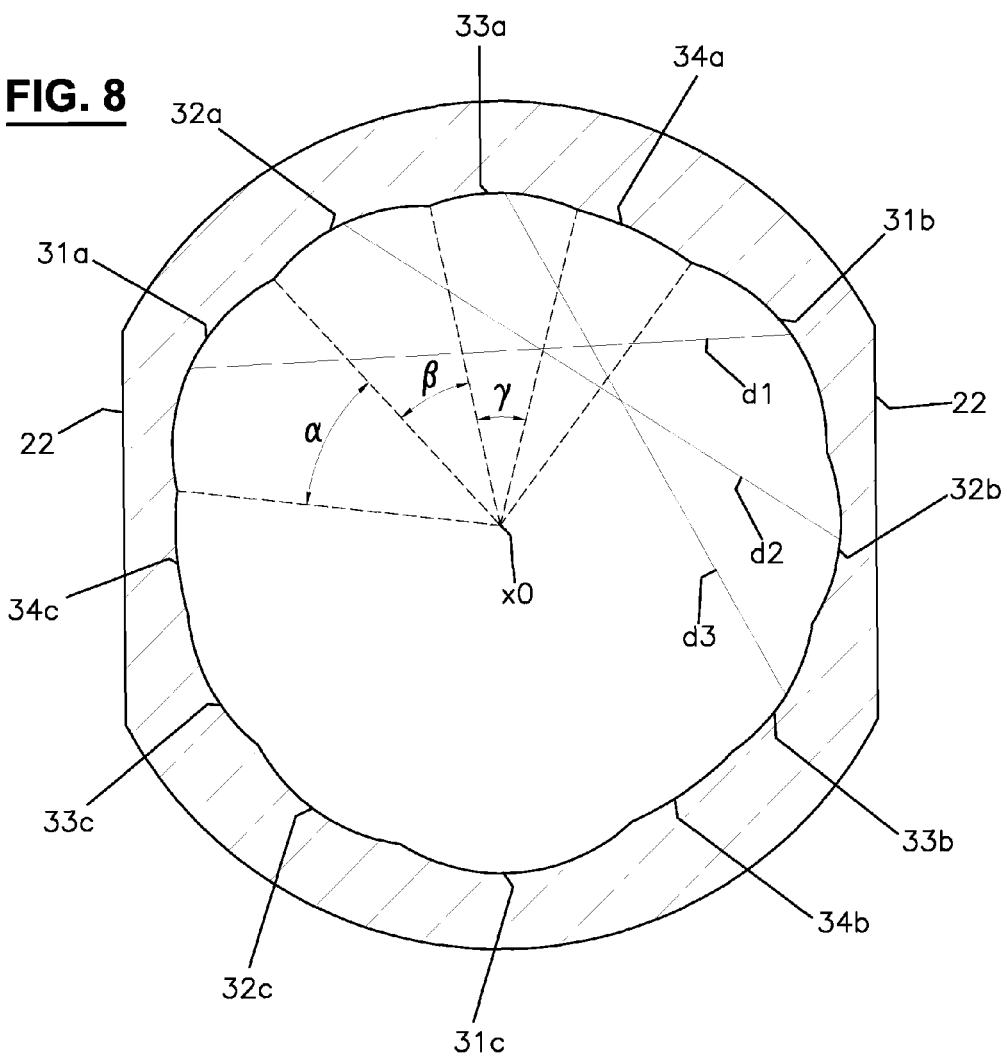
FIG. 8 shows the housing according to FIG. 6 in a section according to line VIII-VIII shown there.

The first inside surface 25b is shaped so that it defines the locking positions of the insert 1 in the housing 20. In general, the inside surface 25b, in a sectional view across the x axis, has a shape different from that of a circular shape. This can be achieved, for example, by providing at least one recess, which has a curvature with a center of curvature that is offset radially from the axis of rotation x. FIG. 8, which is an enlarged view of the housing 20 in cross section, shows an exemplary embodiment. A number of recesses 31a-31c, 32a-32c, 33a-33c are provided, designed so that the extent by which the insert 1 is compressed in the radial direction is different, depending on the angular position of the insert 1 with respect to the housing 20.

In the present example, the housing 20 is designed to receive an insert 1 with three protrusions. The inside surface 25b of the housing 20 has a threefold rotational symmetry, as seen in cross section, i.e., the shape of the inside surface 25b repeats after 120 degrees. In addition, in the present example three locking positions are provided. Thus, the inside surface 25b has a recess of a first type 31a-31c, of a second type 32a-32c and of a third type 33a-33c, as seen over an arc segment of 120 degrees. One of the locations 34a, 34b, 34c is adjacent to the respective recess of the third type 33a-33c and forms the transition to the next 120-degree arc segment.

The recesses of the respective types 31a-31c, 32a-32c, 33a-33c are designed differently. The curvature of the respective recess 31a-31c, 32a-32c, 33a-33 is selected to be the same here, but the maximum distance from the center x0 is varied. Accordingly, the angle range over which a recess of the first type 31a-31c, of the second type 32a-32c, and of the third type 33a-33c extends and the distance between the midpoints of the recesses of the same types 31a-31c, 32a-32c, 33a-33c are different. The angles α, β, γ, about which the recess 31a, 32a and 33a extends, are shown as examples in FIG. 8, which also shows the distances d1, d2, d3 between the midpoints of the recesses 31a and 31b, 32a and 32b and 33a and 33b: Here are α>β>γ and d1>d2>d3.

The recesses 31a-31c, 32a-32c, 33a-33c are formed here as sections of an essentially circular cylindrical surface, but they may also have different shapes, preferably a round shape.

Figure 11:
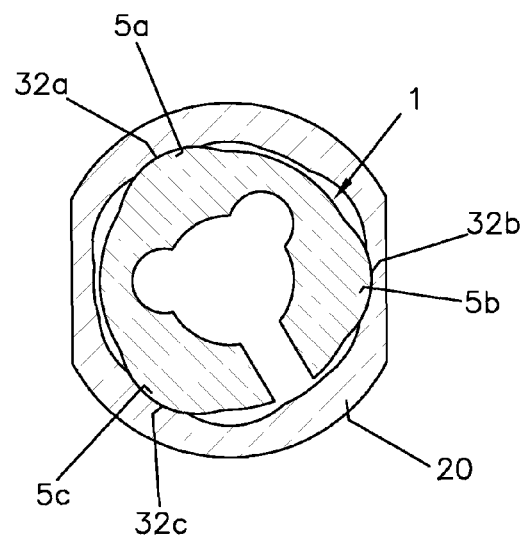
FIG. 11 shows a sectional view according to FIG. 10, but the insert is in the second locking position.
Figure 12:
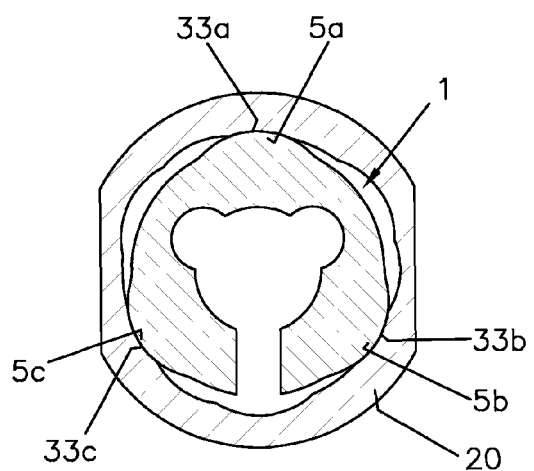
FIG. 12 shows a sectional view according to FIG. 10, but the insert is in the third locking position.

Insert 1 and housing 20 can be combined by aligning the parts relative to one another, so that the protrusions 5a-5c can be inserted over the beveled locations 26a-26c and come to lie in the recesses of the first type 31a-31c. The insert 1 is then situated in the first locking position (cf. FIG. 10). This is designed here, so that the insert 1 essentially assumes the same shape as in the condition separate from the housing 1 and thus the housing 1 exerts practically no additional radial force on the insert 1. If needed, for example, when the holding force with which the female part 1, 20 is held on the male part 50 subsides, the insert 1 is brought into the next locking position by applying a sufficiently great torque to the insert 1, so that the protrusions 5a-5c are moved out of the recesses of the first type 31a-31c and come to lie in the recesses of the second type 32a-32c (cf. FIG. 11). The second locking position is designed so that activation is achieved by the fact that the housing 1 exerts a radial force on the insert 1 and thereby compresses it. The third locking position, which is shown in FIG. 12 and is established by rotating the insert 1 about the x axis again, exhibits an even greater activation here, i.e., the insert 1 is compressed to the greatest extent here. If the insert 1 is rotated once more around the x axis, then it goes from the third locking position past the locations 34a-34c to the first locking position.

Figure 9:
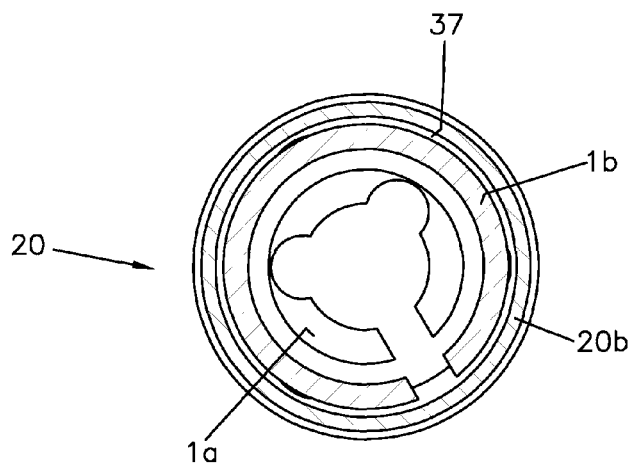
FIG. 9 shows a sectional view of the housing and of the insert according to FIG. 1 in an assembled state, wherein the plane of the section is placed as indicated by the line IX-IX in FIGS. 3 and 6.

The wall element 1b of the insert 1 runs at a distance from the side wall 20b of the housing 20 in the region of the inlet opening, forming a clearance 37 in between (cf. FIGS. 9 and 16). The edge of the insert 1 is thus accessible from the outside, so that it can be compressed as needed, for example, by means of an auxiliary instrument acting on the groove 9, and can be removed from the housing 20.

The female part 1, 20 can be used as a counterpart with a male part 50, for example, as shown in FIGS. 13 through 15. The male part is designed here as an abutment having a connecting end 50a, which is connected via a central male part 50b to a fastening end 50c. The central male part 50b and the fastening end 50c are designed so that the abutment 50 can be fastened to an implant. To this end, the fastening end 50c has a thread, for example, which can be screwed into a complementary thread on the implant.

Depending on the application, the parts 50b and 50c can also be designed so that the male part 50 can be connected with another dental component (root pin, root anchor, bar, in particular a bar manufactured by CAD/CAM, for example, in the form of a male head with a thread by means of which the head can be screwed flush onto the bar, root cap, etc.) or directly in a bone or a dental root.

As shown in FIG. 15 in particular, the connecting end 50a of the male part 50 has a head 51 on the end face with a contour having a convex and/or planar shape. In the present example, the contour has a planar end face 51a, which is adjacent laterally to a circumferential round surface 51b, which has a circular cross section here. The head 51 is preferably free of edges that can disturb a user when it is used in the mouth and/or is free of convex surfaces, in particular depressions, which can make cleaning difficult, among other things. The surface 51b is adjacent to a groove 52 having two side faces 52a and 52c, between which a bottom surface 52b is situated. The side surfaces 52a and 52c are situated toward one another, as seen in cross section, so that the groove 52 tapers in the direction of the bottom surface 52b. As already mentioned above, the head of the male part may also have a different shape, e.g., spherical, conical, etc.

A circumferential collar 54, which is disc-shaped in the present case, is adjacent to the groove 52. This collar 54 protrudes laterally, as can be seen in FIG. 15, and has a larger diameter here than the head 51. The collar 54 is adjacent to the central male part 50b.

The female part comprised of the insert 1 and the housing 20 can be placed on the male part 1 by shifting it in the direction of the x axis. FIG. 16 shows the parts 1, 20, 50 in the assembled state. The head 51 of the male part 50 has been accommodated in the receptacle 10 of the insert 1 and is in contact at least partially with the inner side of the insert 1. The insert 1 thus encloses a part of the male part 1, here the head 51. The collar 54 and the edge of the housing 20 are situated so that the collar 54 is situated outside of the housing 20.

The respective parts 1, 20, 50 are made of a material suitable for use in the mouth, such as a metal, e.g., titanium, or a plastic, e.g., a PEAK (polyaryletherketone), in particular PEEK (polyetheretherketone) or PEKK (polyetherketoneketone). In a special embodiment, the insert 20 is made of an alloy containing gold, with the gold content preferably being greater than 50 weight percent.

Second Exemplary Embodiment

In the first exemplary embodiment, the protrusions 5a-5c as well as the recesses 31a-31c, 32a-32c, 33a-33c at the same time serve as an adjusting mechanism, which cause the insert 1 to undergo a change in the diameter when the insert 1 is rotated with respect to the housing 20, as well as a locking mechanism, by which discretely arranged locking positions can be defined.

It is also conceivable to design the adjusting mechanism and the locking mechanism separately from one another, as is the case with the embodiment described below.

Figure 17:
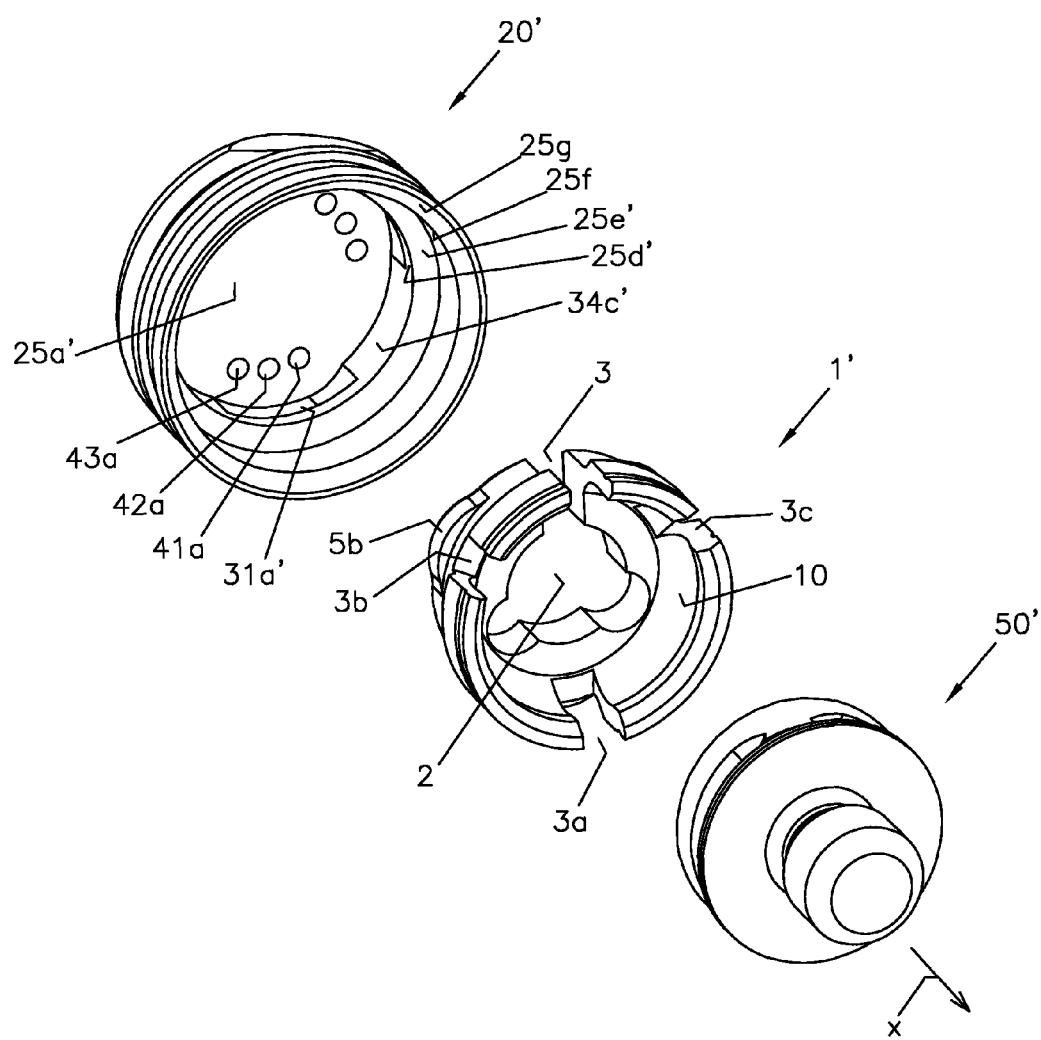
FIG. 17 shows an exploded view of an exemplary male part together with a female part comprising a housing and an insert according to a second exemplary embodiment of the invention.
Figure 18:
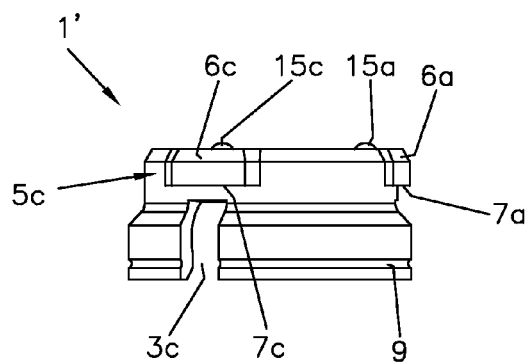
FIG. 18 shows the insert according to FIG. 17 in a side view.
Figure 19:
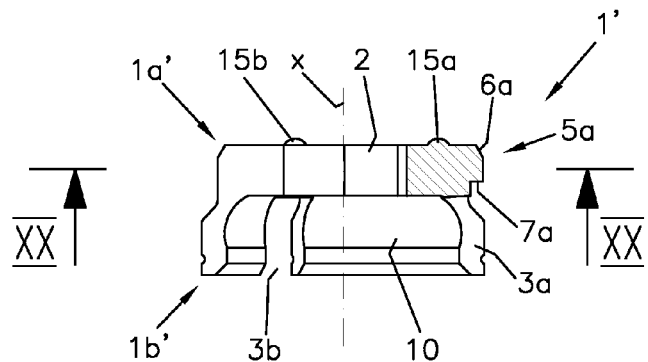
FIG. 19 shows the insert according to FIG. 17 in a longitudinal section, wherein the sectional plane is placed as indicated by the line XIX-XIX in FIG. 20.
Figure 20:
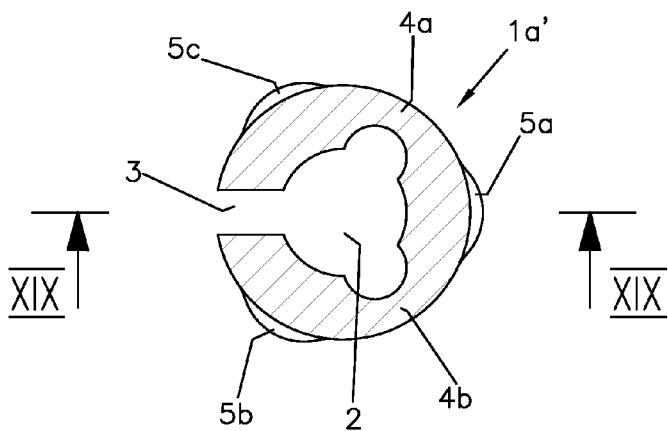
FIG. 20 shows the insert according to FIG. 17 in a cross section, wherein the sectional plane is placed as indicated by the line XX-XX in FIG. 19.
Figure 21:
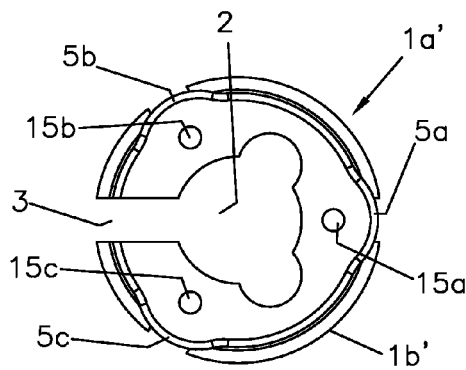
FIG. 21 shows the insert according to FIG. 17 in a view from above.

FIG. 17 shows a second exemplary embodiment of a connecting set having a male part 50' and a female part with a housing 20' and an insert 1'. Elements that are the same as in the first exemplary embodiment are provided with the same reference signs.

The insert 1', which is shown separately in FIGS. 18 through 21, has a cover element 1a', from which a wall element 1b' protrudes, extending around the x axis. In addition to the slot 3 passing through the two elements 1a', 1b', the wall element 1b' is provided with notches 3a, 3b, 3c, so that it has lamellae (cf. FIG. 17).

Figure 22:
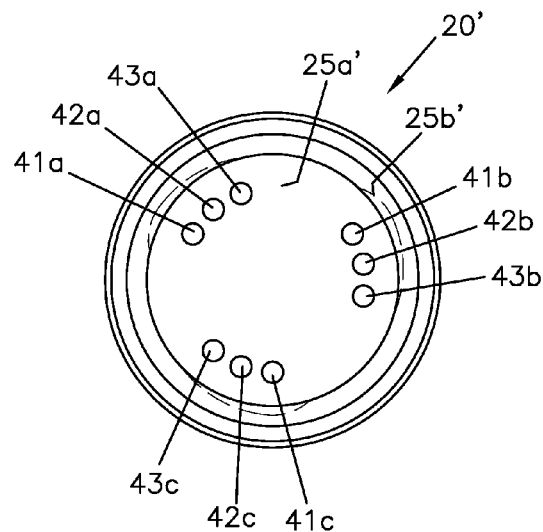
FIG. 22 shows the housing according to FIG. 17 in a view from beneath.
Figure 23:
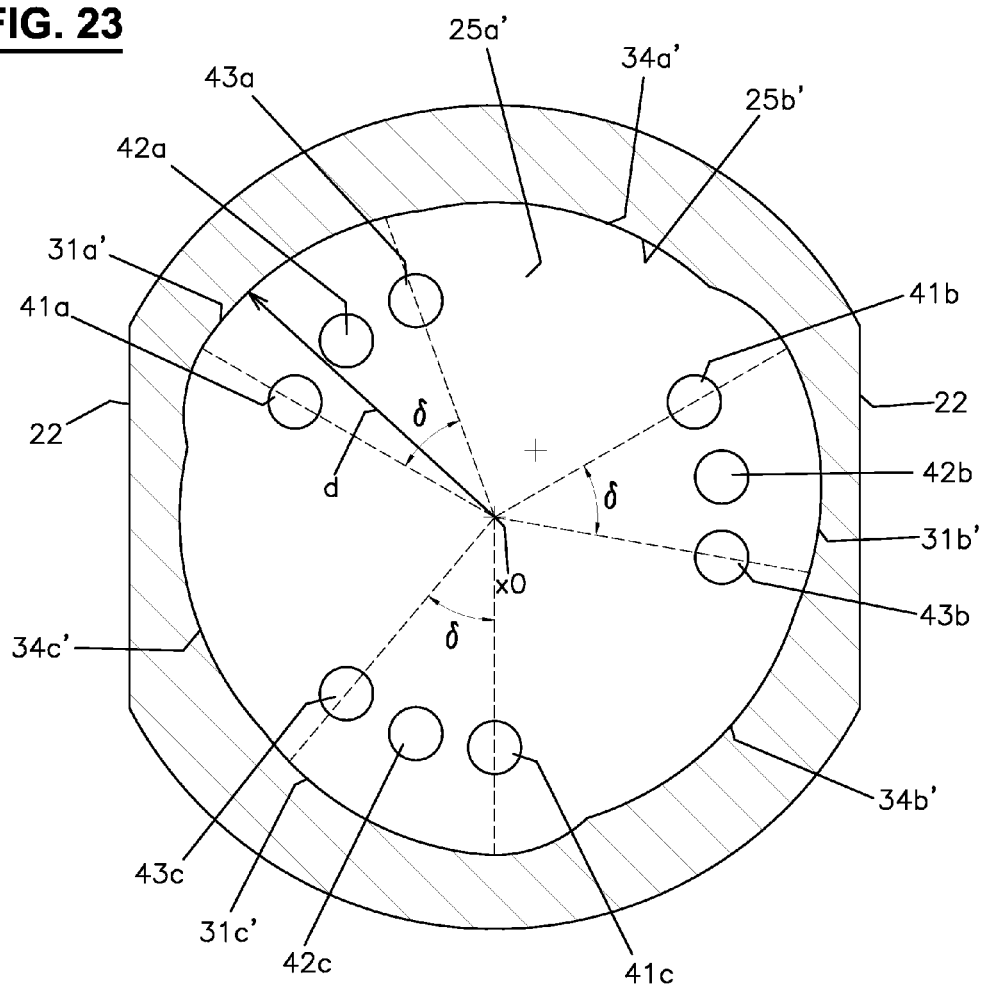
FIG. 23 shows the housing according to FIG. 22 with the sectional view at the level of the housing bottom.

To form the locking mechanism, nubs 15a, 15b, 15c, which protrude out of the base surface and can be engaged in dents 41a-41c, 42a-42c, 43a-43c formed in the bottom 25a' of the housing 20', are arranged on the outside of the cover element 1a' (cf. FIGS. 22 and 23).

Figure 27:
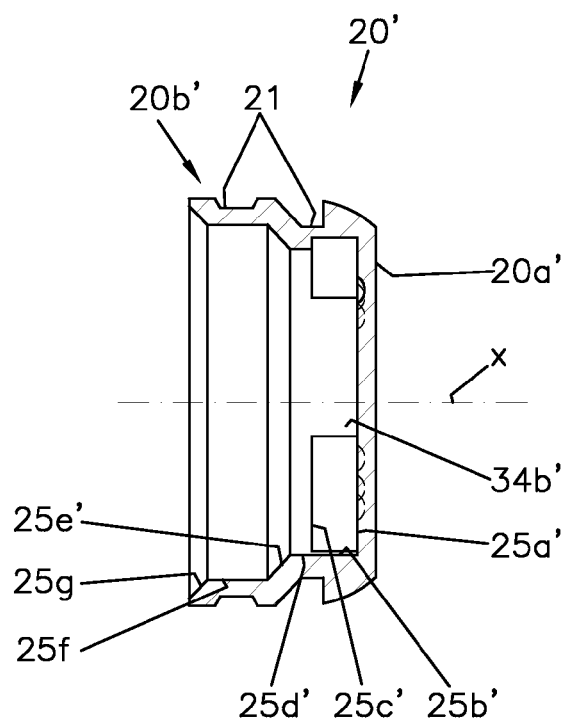
FIG. 27 shows the housing according to FIG. 22 in a sectional side view.

As FIGS. 17 and 27 show, the housing 20' comprises a bottom element 20a' with a side wall 20b' having circumferential inside surfaces 25b'-25d', 25g, 25f, which come after one another as follows, as seen in the direction towards the opening in the housing 20':
  a first inside surface 25b' for contacting the protrusions 5a-5c on the insert 1',
  a second inside surface 25c' arranged transversally to the surface 25b',
  a third inside surface 25d',
  a fourth inside surface 25e' which becomes wider to form a transition to the two other inside surfaces 25f and 25g, which are the same as in the case of the insert 1, according to the first exemplary embodiment.

The second inside surface 25c', which forms an undercut together with the third inside surface 25d', is interrupted at the locations 34a'-34c', which form a transition, where the third inside surface 25d' extends to the bottom 25a'.

The first inside surface 25b' is shaped so that, together with the protrusions 5a-5c on the insert 1', it forms the adjusting mechanism, which make it possible to change the diameter of the insert 1'. In general, the inside surface 25b', in a sectional view across the x axis, has a shape that deviates from a circular shape. FIG. 23 is an enlarged view of the housing 20' in cross section. The inside surface 25b' has recesses 31a'-31c', which have an arc segment extending over an angle δ. In the present example, the housing 20' is designed to receive an insert 1' with three protrusions 5a-5c, so that three identical arc segments δ are provided, each being arranged with a 120 degree radial offset. In addition, an arc segment δ here is designed to be round, the distance d decreasing, as seen in the clockwise direction. Outside of the arc segments δ, the inside surface 25b' has additional curved arc segments, which are preferably designed so that the respective protrusion 5a, 5b, 5c of the insert 1' can be rotated along the entire inside surface 25b'.

In addition, in the present exemplary embodiment, three locking positions are provided, wherein the insert 1' has three nubs. The housing bottom 25a' thus has a triple set of dents, which are offset radially by 120 degrees each. According to FIG. 23, a triple is formed by the dents 41a, 42a, 43a, the dents 41b, 42b, 43b and the dents 41c, 42c, 43c. Depending on the intended application, the number and arrangement of the nubs and the dents can also be selected to be different. In a simpler embodiment, for example, one nub and two dents are provided for predetermining two locking positions. A complementary design is also possible, in which the insert has two or more dents and the housing has one or more nubs.

The arrangement of the dents 41a-43c is selected so as to result in a locking effect, in which, depending on the rotational position of the insert 1' with respect to the housing 20', the protrusions 5a-5c are located on a different location on the arc segment δ and the insert 1' has an altered diameter accordingly. On the whole, this makes the holding force with which the female part 1', 20' is held on the male part 50', precisely adjustable.

Figure 24:
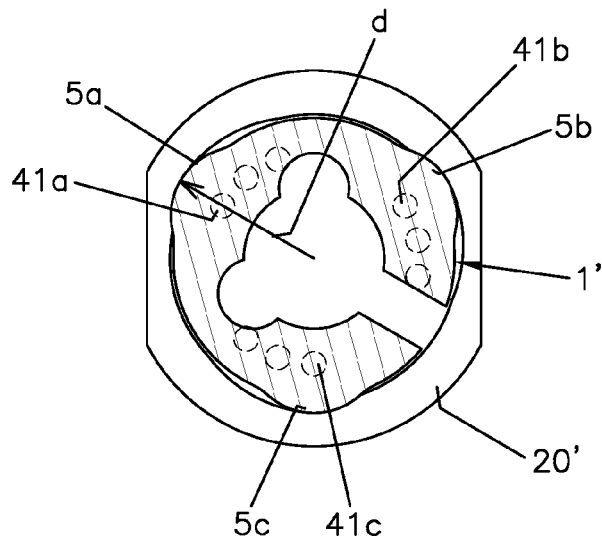
FIG. 24 shows a sectional view of the housing and of the insert which has been inserted into the housing and is in the first locking position according to FIG. 17.
Figure 25:
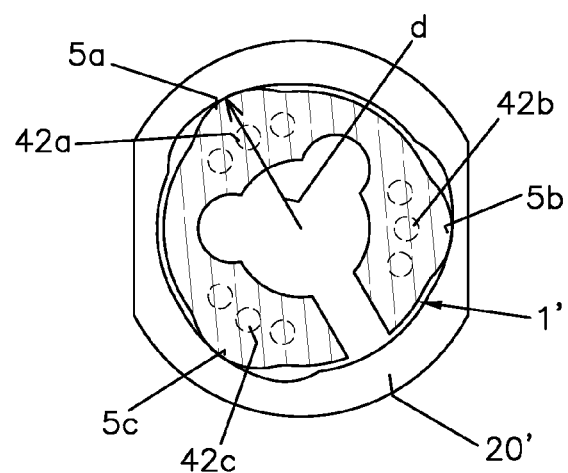
FIG. 25 shows a sectional view according to FIG. 24, but the insert is in the second locking position.
Figure 26:
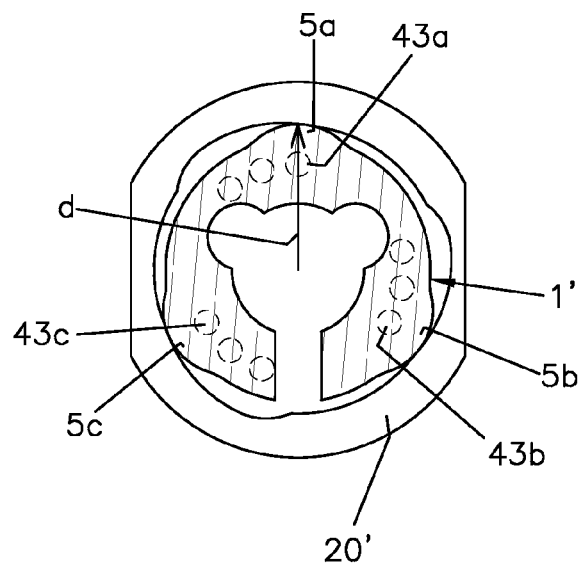
FIG. 26 shows a sectional view according to FIG. 24, but the insert is in the third locking position.

For the present exemplary embodiment, FIGS. 24-26 show the various locking positions of the insert 1': In the first locking position according to FIG. 24, the nubs 15a-15c are situated in the dents 41a-41c; in the second locking position according to FIG. 25, the nubs are in the dents 42a-42c, and in the third locking position according to FIG. 25, the nubs are in the dents 43a-43c. The distance d decreases in each case when the insert 1' is moved from the first locking position to the second and then to the third. The insert 1' is thereby compressed accordingly.

Figure 28:
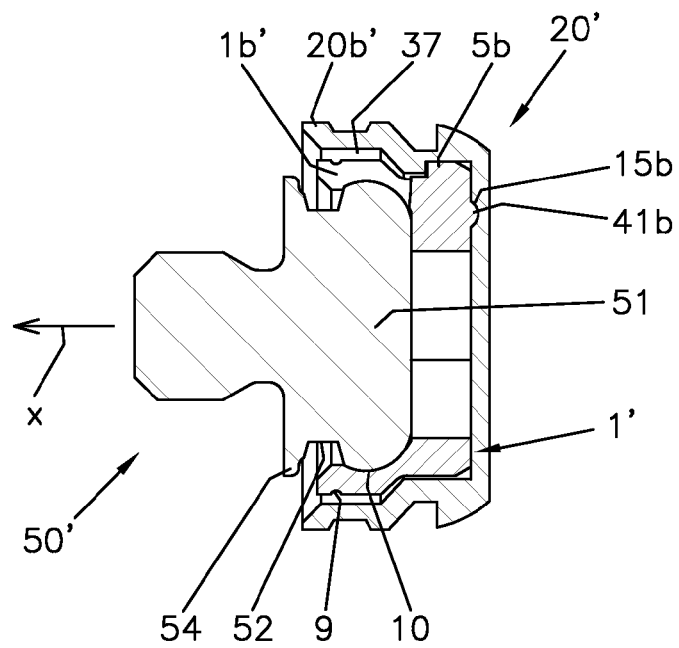
FIG. 28 shows the interconnected parts from FIG. 17 in a longitudinal section.

FIG. 28 shows a cross section through an arrangement in which the insert 1' is inserted into the housing 20' and placed on the head 51 of the male part 50'. The head 51, which is designed to be essentially the same here as in the case of the male part 50 according to FIG. 15, can also be designed differently.

The female parts described here have the advantage that means can be made available easily to adjust the holding force with which the male part is retained and to set it accurately. This is possible solely through suitable shaping of the housing and of the insert without necessarily providing additional parts, as is the case with the known activatable variants.

From the preceding description, numerous modifications are available to those skilled in the art without going beyond the scope of protection of the invention, as defined by the claims.

The adjustment mechanism, which causes a change in the diameter of the insert as a result of the rotation, is situated next to the housing bottom 25a, 25a' in the exemplary embodiments shown above. It is also conceivable for the inner side of the housing and the outer side of the insert to be designed so that the adjusting mechanism is situated on a different level, as seen in the direction of the x axis. For example, it is conceivable to provide a surface of the type as the surface 25b or 25b' at the level of the inside surface 25f according to FIGS. 7 and 27 and to arrange the level of the protrusions 5a-5c on the insert 1 or 1' accordingly with an offset toward the opening.

The embodiments of the female part shown here having three protrusions and three locking positions are just one example. In general, the number, shape and position of the recesses in the housing as well as the nubs and dents—if any—are based on the number of adjustable locking options as well as on the number, shape and position of the protrusions. In a simple embodiment, for example, a single recess and a single protrusion are provided as an adjustment mechanism, and a single nub and two dents are provided as a locking mechanism so that two locking positions are given, in which the insert is compressed to different extents. A complementary arrangement is also possible, in which one or more recesses and/or one or more dents are provided on the outer side of the insert and one or more protrusions and/or one or more nubs are provided on the inner side of the housing.

The inner side of the insert is designed according to the corresponding shape of the male part utilized. Thus, the insert may be designed, for example, so that a different part of the male part than the head can be accommodated therein. For example, the through-opening is shaped so that the head of the male part can be passed through it and can be accommodated in the housing so that, in the assembled state, the insert encloses a region of the male part situated between the two ends.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A female part for forming a releasable connection to a male part that is configured to be fastened in a mouth, the female part comprising:
   a housing, which is configured to be fastened to a dental prosthesis;
   an insert, which is insertable into the housing and rotatable with respect to the housing and which has an inside for receiving a portion of the male part;
   a locking mechanism, which is formed in the housing and on the insert for defining discretely arranged locking positions, the insert being compressed more in at least one locking position than in at least one other locking position; and
   an adjustment mechanism, which is formed in the housing and on the insert and which causes a change in a diameter of the insert when the insert is rotated with respect to the housing,
   wherein the housing has an inner side and the insert has an outer side, and
   wherein for forming the adjusting mechanism, one of the inner side and the outer side comprises at least one protrusion and the other one of the inner side and the outer side comprises at least one recess, with which the at least one protrusion is engageable.

2. The female part according to claim 1, wherein the other one of the inner side and the outer side comprising the at least one recess further comprises an undercut to hold the insert on the housing by retention.

3. The female part according to claim 2, wherein the at least one recess, as seen in a direction in which the insert is insertable into the housing, is arranged behind the undercut.

4. The female part according to claim 1, wherein the adjusting adjustment mechanism is formed without a thread.

5. The female part according to claim 1, wherein the at least one recess has a curvature with a center of curvature that is situated so that it is offset radially relative to an axis of rotation about which the insert is rotatable with respect to the housing.

6. The female part according to claim 1, wherein the at least one recess is formed on the inner side of the housing and the at least one protrusion is formed on the outer side of the insert.

7. The female part according to claim 1, comprising at least two recesses, which, together with the at least one protrusion, serve as the adjustment mechanism and the locking mechanism.

8. The female part according to claim 1, wherein the locking mechanism is different from the adjusting mechanism and comprises at least one nub, which is engageable with dents.

9. The female part according to claim 8, wherein the dents are formed in a bottom of the housing or on an opposite side of the insert, which is opposite to the bottom of the housing when the insert is inserted into the housing.

10. The female part according to claim 1, comprising at least two recesses, which differ in at least one of the following characteristics:
    shape,
    angle range, over which a respective recess extends about an axis of rotation, about which the insert is rotatable with respect to the housing,
    maximum distance from the center of the axis of rotation.

11. The female part according to claim 1, wherein an interspace is formed between the housing and the insert when inserted therein, an auxiliary instrument for handling the insert being insertable into this interspace.

12. The female part according to claim 11, wherein the outer side of the insert comprises at least one groove, which is arranged in the interspace when the insert is inserted into the housing.

13. The female part according to claim 11, wherein the interspace is open toward a front and extends around an axis of rotation, about which the insert is rotatable with respect to the housing.

14. The female part according to claim 1, wherein the insert further comprises, as seen in an direction of an axis of rotation about which the insert is rotatable with respect to the housing, a through-opening, which has a shape configured for a rotationally fixed connection to an auxiliary instrument.

15. The female part according to claim 1, wherein the insert further comprises a through-opening and a wall, which extends around the through-opening and which is continuous or is interrupted by a slot.

16. The female part according to claim 1, wherein the insert comprises a wall with a varying wall thickness to form at least one weakened area.

17. The female part according to claim 16, comprising at least two protrusions, wherein the at least one weakened area is arranged between the at least two protrusions, as seen in a direction of the axis of rotation, about which the insert is rotatable with respect to the housing.

18. The female part according to claim 1, wherein the insert is made of plastic or a metal.

19. The female part according to claim 1, wherein the insert is made of PEAK or a gold alloy.

20. A connecting set for releasable attachment of a dental prosthesis in a mouth, the connecting set comprising:
    a female part for forming a releasable connection to a male part that is configured to be fastened in a mouth, and the male part configured to be connected to the female part;
    the female part comprising:
    a housing, which is configured to be fastened to a dental prosthesis;
    an insert, which is insertable into the housing and rotatable with respect to the housing and which has an inside for receiving a portion of the male part;

a locking mechanism, which is formed in the housing and on the insert for defining discretely arranged locking positions, the insert being compressed more in at least one locking position than in at least one other locking position; and an adjustment mechanism, which is formed in the housing and on the insert and which causes a change in a diameter of the insert when the insert is rotated with respect to the housing, wherein the housing has an inner side and the insert has an outer side, and wherein for forming the adjusting mechanism, one of the inner side and the outer side comprises at least one protrusion and the other one of the inner side and the outer side comprises at least one recess, with which the at least one protrusion is engageable.

21. The connecting set according to claim 20, wherein the male part is formed as an abutment, an implant, a root pin, a root anchor or an element for a bar.

22. The connecting set according to claim 20, wherein the male part terminates, as seen in an axial direction, at a free end defined by an outside surface that has one of a planar shape, a convex shape, and a shape with planar and convex portions.

* * * * *